United States Patent
Balmforth et al.

(10) Patent No.: US 9,856,528 B2
(45) Date of Patent: Jan. 2, 2018

(54) SINGLE NUCLEOTIDE DETECTION METHOD

(71) Applicant: BASE4 INNOVATION LTD, Cambridge, Cambridgeshire (GB)

(72) Inventors: Barnaby Balmforth, Cambridgeshire (GB); Cameron Alexander Frayling, Cambridgeshire (GB)

(73) Assignee: BASE4 INNOVATION LTD, Cambridge, Cambridgeshire (GB)

( * ) Notice: Subject to any disclaimer, the term of this patent is extended or adjusted under 35 U.S.C. 154(b) by 0 days.

(21) Appl. No.: 14/903,174

(22) PCT Filed: Jul. 22, 2015

(86) PCT No.: PCT/GB2015/052119
§ 371 (c)(1),
(2) Date: Jan. 6, 2016

(87) PCT Pub. No.: WO2016/012789
PCT Pub. Date: Jan. 28, 2016

(65) Prior Publication Data
US 2017/0130265 A1    May 11, 2017

(30) Foreign Application Priority Data
Jul. 22, 2014 (GB) .................................. 1412977.9

(51) Int. Cl.
C12Q 1/68 (2006.01)
(52) U.S. Cl.
CPC ......... *C12Q 1/6869* (2013.01); *C12Q 1/6823* (2013.01)
(58) Field of Classification Search
None
See application file for complete search history.

(56) References Cited

U.S. PATENT DOCUMENTS 5,528,046 A    6/1996    Ishikawa

FOREIGN PATENT DOCUMENTS

| JP | 6-148076 | 5/1994 | |
|---|---|---|---|
| WO | 94/18218 | 8/1994 | |
| WO | 03/080861 | 10/2003 | |
| WO | 2014/053854 | 4/2014 | |
| WO | WO 2014053853 A1 * | 4/2014 | ........... C12Q 1/6823 |
| WO | 2014/111723 | 7/2014 | |
| WO | 2014/167323 | 10/2014 | |
| WO | 2014/167324 | 10/2014 | |

OTHER PUBLICATIONS

International Search Report and Written Opinion dated Nov. 9, 2015 in International (PCT) Application No. PCT/GB2015/052119.
Deutscher et al., "Enzymatic Synthesis of Deoxyribonucleic Acid", The Journal of Biological Chemistry, vol. 244, No. 11, Jun. 10, 1969, pp. 3019-3028.
Fan et al., "Highly parallel genomic assays", Nature Review Genetics, vol. 7, 2006, 632-644.
Search Report dated Apr. 22, 2015 in corresponding Great Britain Application No. 1412977.9.

* cited by examiner

*Primary Examiner* — Joseph G. Dauner
(74) *Attorney, Agent, or Firm* — Wenderoth, Lind & Ponack, L.L.P.

(57) ABSTRACT

A method of sequencing a nucleic acid involves (1) generating single nucleoside triphosphates by progressive pyrophosphorolysis of the nucleic acid; (2) producing a substantially double-stranded oligonucleotide used probe by reacting one of the single nucleoside triphosphates with a corresponding probe system comprising (a) a first single-stranded oligonucleotide labelled with characteristic detectable elements in an undetectable state and (b) second and third single-stranded oligonucleotides capable of hybridising to complementary regions on the first oligonucleotide; (3) digesting the used probe with an enzyme having double-stranded exonucleolytic activity to yield the detectable elements in a detectable state and a single-stranded fourth oligonucleotide which is at least in part the complement of the first oligonucleotide; (4) reacting the fourth oligonucleotide with another first oligonucleotide to produce a substantially double-stranded oligonucleotide product corresponding to the used probe; (5) repeating (3) and (4) in a cycle and (6) detecting the detectable elements released in each iteration.

27 Claims, 1 Drawing Sheet

SINGLE NUCLEOTIDE DETECTION METHOD

This invention relates to a method for detecting and characterising single nucleotides which is especially suitable for use in the sequencing of DNA or RNA.

Next generation sequencing of genetic material is already making a significant impact on the biological sciences in general and medicine in particular as the unit cost of sequencing falls in line with the coming to market of faster and faster sequencing machines.

In our previous applications WO 2014/053853, WO 2014/053854, WO2014/167323, WO2014/167324 and WO2014/111723 we have described a new sequencing method which involves progressive digestion of a polynucleotide analyte to generate an ordered stream of single nucleotides, preferably a stream of single deoxyribonucleoside triphosphates, each of which can be captured one-by-one into corresponding droplets in a microdroplet stream. Thereafter, each droplet can be chemically and/or enzymatically manipulated to reveal the particular single nucleotide it originally contained. In one embodiment, these chemical and/or enzymatic manipulations comprise a method involving the use of one or more two-component oligonucleotide probe types each of which is adapted to be able to selectively capture one of the single nucleotide types from which the analyte is constituted. Typically, in each of such probe types, one of the two oligonucleotide components comprises characteristic fluorophores and in the probe's unused state the ability of these fluorophores to fluoresce remains extinguished by virtue of the presence of quenchers located close-by or by self-quenching. In use, when the probe has captured its corresponding single nucleotide, it is rendered susceptible to subsequent exonucleolysis thereby liberating the fluorophores from the quenchers and/or each other enabling them to fluoresce freely. By this means, the original single nucleotide present in each droplet can be identified indirectly by spectroscopic means.

Fan et al in Nature Reviews Genetics 7(8) 632-644 (2006) provide a general review of the development of methods and platforms that have enabled highly parallel genomic assays for genotyping, copy-number measurements, sequencing and detecting loss of heterozygosity, allele-specific expression and methylation. FIG. 2a of this review schematically shows the use of a circularizable probe with 3' and 5' ends that anneal upstream and downstream of a site of single nucleotide polymorphism (SNP) on an analyte thereby leaving a gap which is subsequently filled with a nucleotide which is the complement of the SNP to form a complete circular probe which may then be amplified after release. However unlike our method, the nucleotide which is captured during the filling process is not obtained directly from the analyte itself.

WO03/080861 discloses a process wherein a nucleic acid analyte is subjected to progressive pyrophosphorolysis in the presence of a nucleotide-specific reactive label which attaches directly to the nucleotide as it is released. Not only is this quite different from the method we employ but in practice the fluorescence signal measured when the labelled nucleotides are subsequently interrogated would likely be too weak to enable reliable identification above the associated background noise.

Finally, WO94/18218 teaches a DNA sequencing method in which the analyte is subjected to progressive exonucleolysis to generate a stream of single nucleotide diphosphates or monophosphates which are then incorporated into a fluorescence-enhancing matrix before being detected. Not only is this a completely different approach to the one we describe but we again observe that any signal generated would likely be too weak to be reliably detected and identified.

We have now developed an improved version of the method described in our previous patent applications which has the advantage that each single nucleotide can be caused to give rise to many more free fluorophores than previously obtained thereby making the detection of the associated fluorescence signal above the background noise much easier. As a consequence, the sensitivity of any sequencing device employing the method is greatly improved and the time taken to accurately sequence large nucleic acid molecules (e.g. human DNA fragments) can be shortened considerably. Furthermore, the instrumentation needed for detection is simpler and therefore cheaper to make.

DETAILED DESCRIPTION

Figure 1:
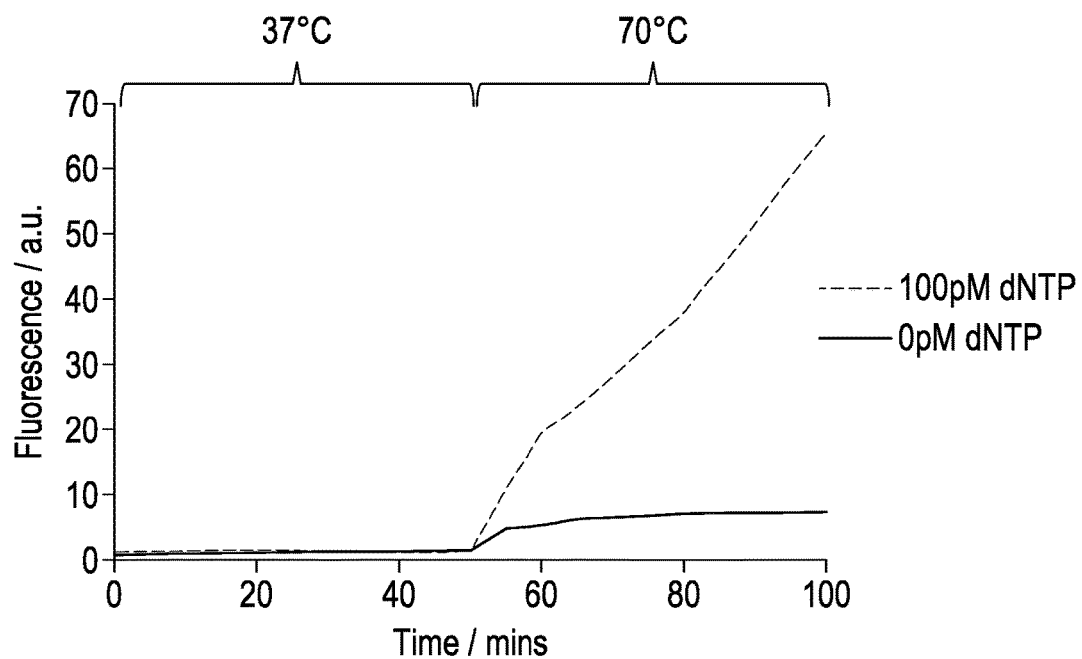
FIG. 1 is a graph showing the growth in intensity of fluorescence over time in the presence and absence of the dNTP component of the reaction mixture.

Thus according to a first aspect of the present invention there is provided a method of sequencing a nucleic acid characterised in that it includes the steps of (1) generating a stream of single nucleoside triphosphates by progressive pyrophosphorolysis of the nucleic acid; (2) producing at least one substantially double-stranded oligonucleotide used probe by reacting in the presence of a polymerase and a ligase at least one of the single nucleoside triphosphates with a corresponding probe system comprising (a) a first single-stranded oligonucleotide labelled with characteristic detectable elements in an undetectable state and (b) second and third single-stranded oligonucleotides capable of hybridising to complementary regions on the first oligonucleotide; (3) digesting the used probe with an enzyme having double-stranded exonucleolytic activity to yield the detectable elements in a detectable state and a single-stranded fourth oligonucleotide which is at least in part the sequence complement of the first oligonucleotide; (4) reacting the fourth oligonucleotide with another first oligonucleotide to produce a substantially double-stranded oligonucleotide product corresponding to the used probe; (5) repeating steps (3) and (4) in a cycle and (6) detecting the characteristic detectable elements released in each iteration of step (3).

Step (1) of the method of the present invention comprises generating a stream of single nucleoside triphosphates from a nucleic acid analyte by pyrophosphorolysis. The analyte employed in this step is suitably a double-stranded polynucleotide the length of which can in principle be unlimited including up to the many millions of nucleotide bases found in a human genome fragment. Typically however the polynucleotide will be at least 50, preferably at least 150 nucleotide pairs long; suitably it will be greater than 500, greater than 1000 and in many cases thousands of nucleotide pairs long. The analyte itself is suitably RNA or DNA of natural origin (e.g. derived from a plant, animal, bacterium or a virus) although the method can also be used to sequence synthetically produced RNA or DNA or other nucleic acids made up wholly or in part of nucleotide bases that are not commonly encountered in nature; i.e. nucleotide bases other than adenine, thymine, guanine, cytosine and uracil. Examples of such nucleotide bases include 4-acetylcytidine, 5-(carboxyhydroxylmethyl)uridine, 2-O—methylcytidine, 5-carboxymethylaminomethyl-2-thiouridine, 5-carboxymethylamino-methyluridine, dihydrouridine, 2-O—methylpseudouridine, 2-O—methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O—methyl-5-methyluridine and 2-O—methyluridine. In the case of DNA the single nucleoside triphosphates generated are deoxyribonucleoside triphosphates whilst in the case of RNA they are ribonucleoside triphosphates.

In one embodiment of the invention, step (1) comprises a first sub-step of attaching the analyte to a substrate. Typically, the substrate comprises a microfluidic surface, a micro-bead or a permeable membrane; for example one made out of glass or a non-degradable polymer. Preferably, the substrate further comprises a surface adapted to receive the analyte. There are many ways in which the analyte can be attached to such surfaces any of which can in principle be used in this sub-step. For example, one method involves priming a glass surface with a functionalised silane such as an epoxysilane, an aminohydrocarbylsilane or a mercaptosilane. The reactive sites so generated can then be treated with a derivative of the analyte which has been modified to include a terminal amine, succinyl or thiol group.

In one embodiment of step (1), the analyte is pyrophosphorolysed to generate a stream of single nucleoside triphosphates the order of which corresponds to that of the sequence of the analyte. Pyrophosphorolysis may be carried out at a temperature in the range 20 to 90° C. in the presence of a reaction medium comprising a polymerase. Preferably it is carried out under conditions of continuous flow so that the single deoxynucleoside triphosphates are continually removed from the reaction zone as they are liberated. Most preferably, the pyrophosphorolysis is carried out by causing an aqueous buffered medium containing the enzyme and the other typical additives to continuously flow over the surface to which the analyte is bound.

In one embodiment, the enzyme used is one which can cause progressive 3'-5' pyrophosphorolytic degradation of the analyte to yield a stream of nucleoside triphosphates with high fidelity and at a reasonable reaction rate. Preferably this degradation rate is as fast as possible and in one embodiment is in the range 1 to 50 nucleoside triphosphates per second. Further information about the pyrophosphorolysis reaction as applied to the degradation of polynucleotides can be found for example in J. Biol. Chem. 244 (1969) pp. 3019-3028. Suitably, the pyrophosphorolytic degradation is carried out in the presence of a medium which further comprises pyrophosphate anion and magnesium cations; preferably in millimolar concentrations.

In step (2) of the method of the present invention at least one single nucleoside triphosphate, preferably each single nucleoside triphosphate in the stream, is reacted in the presence of a polymerase and a ligase with a probe system to generate a substantially double-stranded used probe. Preferably, before this step is carried out the product of step (1) containing the single nucleoside triphosphates is treated with a pyrophosphatase to hydrolyse any residual pyrophosphate to phosphate anion.

The polymerase used in this step is suitably selected from the group consisting of those which show essentially neither exo- nor endonuclease activity under the reaction conditions. Examples of polymerases which can be advantageously used include, but are not limited to, the prokaryotic pol 1 enzymes or enzyme derivatives obtained from bacteria such as *Escherichia coli* (e.g. Klenow fragment polymerase), *Thermus aquaticus* (e.g. Taq Pol), *Bacillus stearothermophilus, Bacillus caldovelox* and *Bacillus caldotenax*. Any suitable ligase can in principle be used in this step.

The probe system employed in step (2) is comprised of three components; (a) a first single-stranded oligonucleotide labelled with characteristic detectable elements in an undetectable state and (b) second and third unlabelled single-stranded oligonucleotides capable of hybridising to complementary regions on the first oligonucleotide. In one embodiment the second and third oligonucleotides are discrete entities whilst in another they are linked to each other by means of a linker region. In this latter case, in one embodiment the linker region links ends of the second and third oligonucleotides; preferably the 5' end of the second and the 3' end of the third oligonucleotide. The linker region can in principle be any divalent group but is conveniently another single- or double-stranded oligonucleotide fragment. In one embodiment the linker region is unable to hybridise substantially to the first oligonucleotide.

The first, second and third oligonucleotides are chosen so that in step (2) the second and third oligonucleotides can hybridise respectively to 3' side and 5' side flanking regions on the first oligonucleotide which themselves are juxtaposed either side of a capture region which comprises the single nucleotide whose nucleotide base is complementary to the one borne by the nucleoside triphosphate to be detected. This makes the three-component probe system highly selective for that particular nucleoside triphosphate. Thus, for example, if the analyte is derived from DNA and the first, second and third oligonucleotides are deoxyribonucleotides, the capture region will be highly selective for deoxyadenosine triphosphate if the nucleotide it comprises bears a thymine base. In one useful embodiment of the invention, step (2) may be carried out in the presence of a plurality of probe system types; for example one, two, three or four probe system types each of which comprises a first oligonucleotide having a different capture region characteristic of the various different nucleotide bases sought and different detectable elements attached thereto.

Typically, the first oligonucleotide is up to 150 nucleotides long, preferably between 20 and 100 nucleotides. In one embodiment the second oligonucleotide is longer than the complementary 3' side flanking region of the first oligonucleotide by up to 10 preferably from 1 to 5 nucleotides. In another, there is a single nucleotide mismatch between the 3' end of the first oligonucleotide and the nucleotide opposite it on the second oligonucleotide to prevent the nucleoside triphosphate being captured by the polymerase at this point. In yet another embodiment the 3' end of the third oligonucleotide includes an element resistant to exonucleolytic degradation to ensure that the fourth oligonucleotide produced in step (3) is not itself subsequently digested. This can be achieved for example by way of incorporating one or more phosphorothioate linkages, a G-Quadruplex, a boronated nucleotide, an inverted dT or ddT, a C3 spacer or a phosphate group at or near that particular end.

It is a feature of the first oligonucleotide that it is multiply labelled with its own unique type of detectable element(s) and that these detectable elements are substantially undetectable when the probe system is in an unused state. Suitably these detectable elements are ones adapted to be detected after an optical event has taken place. In one preferred embodiment, the detectable elements comprise fluorophores and each unused first oligonucleotide is essentially non-fluorescing at those wavelengths where the fluorophores are designed to be detected. Thus, although a fluorophore may exhibit general, low-level background fluorescence across a wide part of the electromagnetic spectrum, there will typically be one or a small number of specific wavelengths or wavelength envelopes where the intensity of the fluorescence is at a maximum. It is at one or more of these maxima where the fluorophore is characteristically detected that essentially no fluorescence should occur. In the context of this patent, by the term 'essentially non-fluorescing' or equivalent wording is meant that the intensity of fluorescence of the total number of fluorophores attached to the first oligonucleotide at the relevant characteristic wavelength or wavelength envelope is less than 25%; preferably less than 10%; more preferably less than 1% and most preferably less than 0.1% of the corresponding intensity of fluorescence of an equivalent number of free fluorophores.

In principle, any method can be used to ensure that in the first oligonucleotide's unused state the fluorophores are essentially non-fluorescing. One approach is to additionally attach quenchers in close proximity to them. Another is based on the observation that when multiple fluorophores are attached to the first oligonucleotide in close proximity to each other they tend to quench each other sufficiently well that the criterion described in the previous paragraph can be achieved without the need for quenchers. In this context of this patent, what constitutes 'close proximity' between fluorophores or between fluorophores and quenchers will depend on the particular fluorophores and quenchers used and possibly the structural characteristics of the first oligonucleotide. Consequently, it is intended that this term should be construed with reference to the required outcome rather than any particular structural arrangement of the various elements. However, and for the purposes of providing exemplification only, it is pointed out that when adjacent fluorophores or adjacent fluorophores and quenchers are separated by a distance corresponding to the characteristic Förster distance (typically less than 5 nm) sufficient quenching will generally be achieved.

Suitably the first oligonucleotide is labelled with at least 1, preferably up to 20 fluorophores. To obtain maximum advantage, it is preferred that the first oligonucleotide is labelled with at least 2 preferably at least 3 fluorophores. Consequently, ranges constructed from any permutation of these maxima and minima are specifically envisaged herein. If quenchers are employed, it is likewise preferred that the first oligonucleotide is labelled with up to 20, preferably up to 10 and most preferably up to 5 of the same.

As regards the fluorophores themselves, they can in principle be chosen from any of those conventionally used in the art including but not limited to xanthene moieties e.g. fluorescein, rhodamine and their derivatives such as fluorescein isothiocyanate, rhodamine B and the like; coumarin moieties (e.g. hydroxy-, methyl- and aminocoumarin) and cyanine moieties such as Cy2, Cy3, Cy5 and Cy7. Specific examples include fluorophores derived from the following commonly used dyes: ALEXA dyes, cyanine dyes, ATTO TEC dyes, and rhodamine dyes. Examples also include: ATTO 633 (ATTO-TEC GmbH), TEXAS RED™, ATTO 740 (ATTO-TEC GmbH), Rose Bengal, ALEXA FLUOR™750 $C_5$-maleimide (Invitrogen), ALEXA FLUOR™532 $C_2$-maleimide (Invitrogen) and Rhodamine Red $C_2$-maleimide and Rhodamine Green as well as phosphoramadite dyes such as QUASAR 570. Alternatively, a quantum dot or a near infra-red dye such as those supplied by LI-COR Biosciences can be employed. The fluorophore is typically attached to the first oligonucleotide via a nucleotide base using chemical methods known in the art.

Suitable quenchers include those which work by a Förster resonance energy transfer (FRET) mechanism. Examples of commercially available quenchers which can be used in association with the above mentioned-fluorophores include but are not limited to DDQ-1, DABCYL, ECLIPSE, IOWA BLACK FQ and RQ, IR Dye-QC1, BHQ-0, BHQ-1, -2and -3 and QSY-7 and -21.

In one embodiment the second and third oligonucleotides are not labelled with detectable elements.

Step (2) is suitably carried out by contacting each single nucleoside triphosphate in the stream with one or more probe systems as described above at a temperature in the range 20 to 80° C.

The product of step (2) of the method of the invention is, as mentioned above, a substantially double-stranded used probe whose constituent strands are respectively the first oligonucleotide and a complementary fourth oligonucleotide which when read in its 5'-3' direction is comprised of the second oligonucleotide, then a nucleotide derived from the single nucleoside triphosphate and finally the third oligonucleotide. If the second and third oligonucleotides have previously been joined together by a linker region then it will be readily apparent that the fourth oligonucleotide will comprise a closed loop strand that is highly resistant to exonucleolysis.

In Step (3) the used probe is treated with an enzyme at a temperature in the range 30 to 100° C. In this step the strand of the used probe derived from the first oligonucleotide is digested into its constituent nucleotides (deoxyribonucleoside monophosphates or ribonucleoside monophosphates as the case may be) in the process separating the detectable elements from one another and thereby causing them to become unquenched and therefore detectable. Thus if the detectable elements are fluorophores which have been quenched into an undetectable state in the first oligonucleotide, step (3) will liberate the fluorophores from each other and any quenchers thereby causing them fluorescence. As the digestion process occurs the observer therefore sees rapid growth in the fluorescence signal as a cascade of single nucleotides is generated. The characteristics of this fluorescence then indirectly reflect the nature of the single nucleoside triphosphate originally captured by the relevant probe system.

Enzymes which can be used in step (3) comprise exonucleases or polymerases which exhibit 3'-5' exonucleolytic activity. This class of enzyme includes Q5, Q5HOT START, PHUSION, PHUSION HS, PHUSION II, PHUSION II HS, Dnase I (RNase-free), Exonuclease I or III (ex *E.coli*), Exonuclease T, Exonuclease V (RecBCD), Lambda Exonuclease, Micrococcal Nuclease, Mung Bean Nuclease, Nuclease BAL-31, RecJ$_f$, T5 Exonuclease and T7 Exonuclease.

In one embodiment at the end of step (3) the reaction mixture is cycled between relatively high and relatively low temperatures in order to remove any residual oligonucleotide fragments left over from the first oligonucleotide from the fourth oligonucleotide and to allow new second and third oligonucleotides to anneal.

In step (4) the fourth oligonucleotide now present in single-stranded form is caused to hybridise to another first oligonucleotide molecule thereby producing a new substantially double-stranded oligonucleotide product corresponding to, i.e. having the same chemical and physical structure as the used probe. This product is then digested in a repeat of step (3) thereby releasing further detectable elements in a detectable state and again regenerating the fourth oligonucleotide. Thereafter, according to step (5), steps (3) and (4) are allowed to continue in a cyclic way causing further enhancement in the signal from the free detectable elements e.g. the fluorescence signal; in principle until substantially all of the first oligonucleotide has been consumed. As a consequence the observer sees a much greater enhancement of the fluorescence signal than has been previously obtained.

Thereafter, and in step (6), the detectable elements liberated in the various iterations of step (3) are detected and the nature of the nucleotide base attached to the single nucleoside triphosphate determined. By carrying out the method of the invention systematically for all the single nucleoside triphosphates in the stream generated in step (1), data characteristic of the sequence of the original nucleic acid analyte can be generated and analysed. Methods of doing this are well-known in the art; for example fluorescence may be detected using a photodetector or an equivalent device tuned to the characteristic fluorescence wavelength(s) or wavelength envelope(s) of the various fluorophores. This in turn causes the photodetector to generate a characteristic electrical signal which can be processed and analysed in a computer using known algorithms. In one embodiment, a period of time is allowed to elapse between steps (5) and (6) to ensure that the number of detectable elements in a detectable state has grown to a maximum.

In one particularly preferred embodiment, the method of the present invention is carried out wholly or partially in a stream of microdroplets, at least some of which contain a single nucleoside triphosphate; suitably an ordered stream. Such a method may begin, for example, by inserting the nucleoside triphosphates generated in step (1) one-by-one into a corresponding stream of aqueous microdroplets maintained in an immiscible carrier solvent such as a hydrocarbon or silicone oil to help preserve the ordering. Advantageously, this can be achieved by directly creating the microdroplets downstream of the pyrophosphorolysis reaction zone; for example by causing the reaction medium to emerge from a microdroplet head of suitable dimensions into a flowing stream of the solvent. Alternatively, small aliquots of the reaction medium from step (1) can be regularly and sequentially injected into a stream of pre-existing aqueous microdroplets suspended in the solvent. If this latter approach is adopted, each microdroplet may already contain the various components of the probe system(s) together with the enzymes and any other reagents (e.g. buffer) required to effect steps (2) to (5). In yet another approach, the microdroplets created in the former embodiment can be caused to coalesce subsequently with a stream of such pre-existing microdroplets to achieve a similar outcome. In these microdroplet methods, step (6) then preferably involves interrogating each microdroplet to identify the detectable elements liberated and hence the nature of the nucleoside triphosphate it originally contained.

To avoid the risk that a given microdroplet contains more than one nucleoside triphosphate it is preferred to release each nucleoside triphosphate in step (1) at a rate such that each filled microdroplet is separated by from 1 to 20 preferably 2 to 10 empty ones. Thereafter the stream of filled and unfilled microdroplets in the solvent is caused to flow along a flow path, suitably a microfluidic flow path, at a rate and in a manner such that they are maintained in a discrete state and do not have the opportunity to coalesce with each other. Suitably the microdroplets employed have a finite diameter less than 100 microns, preferably less than 50 microns, more preferably less than 20 microns and even more preferably less than 15 microns. Most preferably of all their diameters are in the range 2 to 20 microns. In one embodiment, the microdroplet flow rate through the whole system is in the range 50 to 3000 microdroplets per second preferably 100 to 2000.

According to a second aspect of the invention there is provided a probe system characterised by comprising (a) a first single-stranded oligonucleotide labelled with one or more fluorophores in an undetectable state and (b) second and third unlabelled single-stranded oligonucleotides capable of hybridising respectively to complementary 3' side and 5' side flanking regions on the first oligonucleotide which are juxtaposed either side of a single nucleotide capture region the length of the second oligonucleotide being at least one nucleotide longer than the 3' side flanking region.

In a first embodiment of this aspect of the invention the second and third oligonucleotides are linked by a linker region typically a single- or double-stranded oligonucleotide region. In another embodiment the nucleotide at the 3' end of the first oligonucleotide is a mismatch with the corresponding nucleotide in the second oligonucleotide. In yet another, the third oligonucleotide includes an element resistant to exonucleolytic degradation at its 3' end. In another embodiment of the invention the fluorophores are located in the 5' flanking region of the first oligonucleotide which may also include quenchers.

The method and probe systems described above can be used to advantage in a sequencing device and such devices are envisaged as being within the scope of the invention.

The present invention in its various aspects will now be illustrated with reference to the following examples.

EXAMPLE 1

Preparation and Use of a Probe System

A single-stranded first oligonucleotide 1 was prepared, having the following nucleotide sequence:

(SEQ ID NO: 1)
5'TCGTGCCTCATCGAACATGACGAGGXXQXXGGTTTGTGGT3' wherein A, C, G, and T represent nucleotides bearing the relevant characteristic nucleotide base of DNA; X represents a deoxythymidine nucleotide (T) labelled with ATTO 655 dye using conventional amine attachment chemistry and Q represents a deoxythymidine nucleotide labelled with a BHQ-2quencher. It further comprises a capture region (A nucleotide) selective for capturing deoxythymidine triphosphate nucleotides (dTTPs) in a mixture of deoxynucleotide triphosphates (dNTPs).

Another single-stranded oligonucleotide 2, comprising (1) a second oligonucleotide region having a sequence complementary to the 3' end of the first oligonucleotide with a single base mismatch; (2) a third oligonucleotide region having a sequence complementary to the 5' end of the first oligonucleotide and (3) a 76base pair single-stranded linker region, was also prepared. It had the following nucleotide sequence:

(SEQ ID NO: 2)
5'PCATGTTCGATGAGGCACGATAGATGTACGCTTTGACATACGCTTTGA

CAATACTTGAGCAGTCGGCAGATATAGGATGTTGCAAGCTCCGTGAGTCC

CACAAACCAAAAACCTCG3' wherein additionally P represents a 5' phosphate group.

A reaction mixture comprising the probe system was then prepared. It had a composition corresponding to that derived from the following formulation:
  56 uL 5×buffer pH 7.5
  28 uL oligonucleotide 1, 100 nM
  28 uL oligonucleotide 2, 10 nM
  2.8 uL mixture of dNTPs (including dTTP), 10 nM
  0.4 U PHUSION II HOT START polymerase (exonuclease)
  1.6 U Bst Large Fragment polymerase
  20 U E. coli ligase
  4 U Thermostable Inorganic Pyrophosphatase
  Water to 280 uL
wherein the 5×buffer comprised the following mixture:
  200 uL Trizma hydrochloride, 1M, pH 7.5
  13.75 uL aqueous $MgCl_2$, 1M
  2.5 uL Dithiothreitol, 1M
  50 uL TRITON X-100 surfactant (10%)
  20 uL Nicotinamide adenine dinucleotide, 100 uM
  166.67 uL KCl
  Water to 1 mL Capture of the dTTPs and ligation of oligonucleotide 2 to oligonucleotide 1 to form a closed-loop used probe was then carried out by incubating the mixture at 37° C. for 50 minutes after which the temperature was increased to 70° C. for a further 50 minutes. The reaction mixture was then illuminated using the 633 nm line of a Helium-Neon laser and the resulting characteristic fluorescence of the ATTO 655 dye detected using a camera as the cycle of exonucleolysis and regeneration of the used probe began.

The growth in intensity of fluorescence over time in the presence and absence of the dNTP component of the reaction mixture was monitored and the results shown graphically in FIG. 1. From this it can be seen that the probe system efficiently captures the dTTPs and the cyclic nature of the process of the present invention leads to a rapid growth in fluorescence signal. On the contrary, in a comparative experiment where no dNTPs were present, the ATTO 655 dye on oligonucleotide 1 did not exhibit fluorescence to any significant extent.

EXAMPLE 2

Droplet Microfluidic Method Using the Probe System

Figure 2:
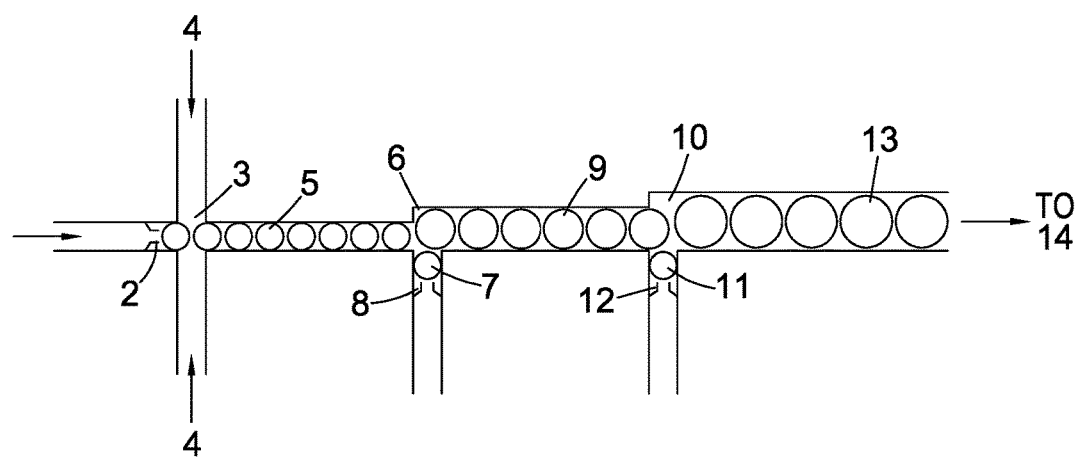
FIG. 2 schematically illustrates a microfluidic sequencing device in which microdroplets each containing a single nucleotide base are made to undergo reaction with a probe system.

FIG. 2 schematically illustrates a microfluidic sequencing device in which microdroplets each containing a single nucleotide base are made to undergo reaction with a probe system of the type above as described above.

An aqueous medium 1 comprising a stream of single nucleotide triphosphates obtained by the progressive pyrophosphorolysis of a 100 nucleotide base polynucleotide analyte derived from human DNA is caused to flow through a ten micron diameter microfluidic tube fabricated from PDMS polymer. The pyrophosphorolysis reaction itself is carried out by passing a stream of an aqueous, buffered (pH 7.5) reaction medium at 72° C., comprising Taq Pol and a solution having a 2 millimoles per liter concentration of each of sodium pyrophosphate and magnesium chloride, over a glass micro bead onto which the analyte has been previously attached by means of a succinyl bridge. The order of the single nucleotides in 1, which is downstream of the micro bead, corresponds to the sequence of the analyte. 1 emerges from a droplet head 2 into a first chamber 3 where it is contacted with one or more streams of immiscible light silicone oil 4. The velocities of these streams are chosen to avoid turbulent mixing and to create aqueous spherical droplets 5 suspended in the oil each having a diameter of approximately eight microns. Typically, rates are adjusted so that between adjacent filled droplets there are 10 empty ones. A stream of 5 is then carried forward along a second microfluidic tube of the same diameter to a second chamber 6 into which a second stream of five micron aqueous spherical droplets 7 is also fed by means of a second droplet head 8. Droplets 5 and 7 are caused to coalesce in a sequential fashion to form enlarged aqueous droplets 9 approximately nine microns in diameter. Each of 7 contains pyrophosphatase to destroy any residual pyrophosphate anion present in each of 5.

A stream of 9 is then carried forward at the same rate via microfluidic tubing into a third chamber 10 where these droplets are contacted with a third stream of five micron aqueous spherical droplets 11 also fed thereto through a corresponding droplet head 12. The time taken for each of 9 to move between chambers 6 and 10 is c.2minutes.

Droplets 9 and 11 are then caused to coalesce in 10 to produce droplets 13 (approximately ten microns in diameter). Each of 11 contains a mesophilic ligase, a thermophilic polymerase exhibiting 3'-5' double-stranded exonuclease activity and a probe system comprising four pairs of single-stranded oligonucleotides similar to those described in Example 1. Each first oligonucleotide is 40 nucleotides long and has a different $20^{th}$ nucleotide (measured from the 5' end) characteristic of the four characteristic nucleotide base types of DNA (i.e. A, T, G and C). Each first oligonucleotide is also labelled with multiple fluorophores and quenchers in close proximity to each other such that in their bound-together state they are essentially non-fluorescing and when released they fluoresce at a wavelength characteristic of the first oligonucleotide from which they are derived. The four different second oligonucleotides are each 115 nucleotide bases long, have different terminating sequences at their two ends which are complementary to the regions flanking the $20^{th}$ bases of the first oligonucleotides, and have a common 76 base pair linker region.

The stream of the coalesced microdroplets 13 so formed is then subjected to incubation at 37° C. for 30 minutes followed by 70° C. for 30 minutes. At the end of this time 13 is transferred to the detection system, 14.

The detection system (not shown) typically comprises a detection window in which each droplet is interrogated with incident light from a laser. Action of this light then causes the released fluorophores in each droplet to fluoresce in a way characteristic of the single nucleotide base which was originally incorporated into the captured molecule (or essentially not at all if the droplet was originally empty). The presence or absence of this fluorescence is then detected at the four characteristic wavelengths of the four fluorophores mentioned above. Thus as the droplets are interrogated in turn the sequence of nucleotide bases in the original polynucleotide analyte can in effect be read off.

The invention claimed is:

1. A method of sequencing a nucleic acid, comprising the steps of:
   (1) generating an ordered stream of single nucleoside triphosphates by progressive pyrophosphorolysis of the nucleic acid;
   (2) producing at least one double-stranded oligonucleotide used probe by reacting in the presence of a polymerase and a ligase each single nucleoside triphosphate in the ordered stream with a probe system comprising (a) a first single-stranded oligonucleotide having a nucleoside capture region and labelled with detectable elements in an undetectable state and (b) second and third single-stranded oligonucleotides capable of hybridising to complementary regions on the first oligonucleotide, wherein the third oligonucleotide is exonuclease resistant;
   (3) digesting the used probe with an enzyme having double-stranded exonucleolytic activity to yield the detectable elements in a detectable state and a single-stranded fourth oligonucleotide which is at least in part the sequence complement of the first oligonucleotide;
   (4) reacting the fourth oligonucleotide with another molecule of the first oligonucleotide of the probe system to produce a double-stranded oligonucleotide product corresponding to the used probe;
   (5) repeating steps (3) and (4) in a cycle and (6) detecting the detectable elements released in each iteration of step (3).

2. The method as claimed in claim 1 wherein the nucleoside capture region is complementary to the single nucleoside triphosphate to be captured and in that the nucleoside capture region is flanked by regions which are complementary to the second and third oligonucleotides.

3. The method as claimed in claim 2 wherein the detectable elements are located on the first oligonucleotide between its 5' end and the nucleoside capture region.

4. The method as claimed in claim 2 wherein the second oligonucleotide (a) hybridises to the flanking region on the 3' side of the nucleoside capture region and (b) is longer than the region on said side.

5. The method as claimed in claim 1 wherein the 3' end of the third oligonucleotide includes an element resistant to exonucleolytic degradation.

6. The method as claimed in claim 1 wherein there is an at least one nucleotide base mismatch between the 3' end of the first oligonucleotide and the corresponding region of the second oligonucleotide.

7. The method as claimed in claim 1 wherein the detectable elements attached to the first oligonucleotide comprise fluorophores.

8. The method as claimed in claim 7 wherein the fluorophores are rendered undetectable in the first oligonucleotide by the presence of at least one quencher.

9. The method as claimed in claim 1 which comprises cycling the temperature of step (3) to remove any residual oligonucleotide fragments attached to the fourth oligonucleotides after the detectable elements have been released and to allow a new molecule of the first oligonucleotide to anneal.

10. The method as claimed in claim 1 wherein the probe system comprises a plurality of first oligonucleotide types each provided with a different nucleoside capture region, different detectable elements and oligonucleotide regions flanking the nucleoside capture region able to hybridises selectively to different corresponding second and third oligonucleotides within its particular probe type.

11. The method as claimed in claim 10 wherein up to four different sets of oligonucleotide probe systems are employed, the first oligonucleotide of each set having a nucleoside capture region selective for one of the nucleotide bases of naturally-occurring DNA or RNA and different detectable elements.

12. The method as claimed in claim 1 wherein step (1) further comprises containing each single nucleoside triphosphate in a corresponding microdroplet and steps (2) to (6) are carried out on each microdroplet.

13. The method as claimed in claim 12 wherein the results obtained by step (6) are assembled into a stream of data characteristic of the sequence of the nucleic acid.

14. A method of sequencing a nucleic acid, comprising the steps of:
(1) generating an ordered stream of single nucleoside triphosphates by progressive pyrophosphorolysis of the nucleic acid;
(2) producing at least one double-stranded oligonucleotide used probe by reacting in the presence of a polymerase and a ligase each single nucleoside triphosphate in the ordered stream with a probe system comprising (a) a first single-stranded oligonucleotide having a nucleoside capture region and labelled with detectable elements in an undetectable state and (b) second and third single-stranded oligonucleotides capable of hybridising to complementary regions on the first oligonucleotide, wherein the 5' end of the second oligonucleotide and the 3' end of the third oligonucleotide are connected by a linker region;
(3) digesting the used probe with an enzyme having double-stranded exonucleolytic activity to yield the detectable elements in a detectable state and a single-stranded fourth oligonucleotide which is at least in part the sequence complement of the first oligonucleotide;
(4) reacting the fourth oligonucleotide with another molecule of the first oligonucleotide of the probe system to produce a double-stranded oligonucleotide product corresponding to the used probe;
(5) repeating steps (3) and (4) in a cycle and
(6) detecting the detectable elements released in each iteration of step (3).

15. The method as claimed in claim 14 wherein the linker region comprises an oligonucleotide region.

16. The method as claimed in claim 14 wherein the fourth oligonucleotide generated comprises a closed loop.

17. The method as claimed in claim 14 wherein nucleoside capture region is complementary to the single nucleoside triphosphate to be captured and in that the nucleoside capture region is flanked by regions which are complementary to the second and third oligonucleotides.

18. The method as claimed in claim 17 wherein the detectable elements are located on the first oligonucleotide between its 5' end and the nucleoside capture region.

19. The method as claimed in claim 17 wherein the second oligonucleotide (a) hybridises to the flanking region on the 3' side of the nucleoside capture region and (b) is longer than the region on said side.

20. The method as claimed in claim 14 wherein there is an at least one nucleotide base mismatch between the 3' end of the first oligonucleotide and the corresponding region of the second oligonucleotide.

21. The method as claimed in claim 14 wherein the detectable elements attached to the first oligonucleotide comprise fluorophores.

22. The method as claimed in claim 21 wherein the fluorophores are rendered undetectable in the first oligonucleotide by the presence of at least one quencher.

23. The method as claimed in claim 14 which comprises cycling the temperature of step (3) to remove any residual oligonucleotide fragments attached to the fourth oligonucleotides after the detectable elements have been released and to allow a new molecule of the first oligonucleotide to anneal.

24. The method as claimed in claim 14 wherein the probe system comprises a plurality of first oligonucleotide types each provided with a different nucleoside capture region, different detectable elements and oligonucleotide regions flanking the nucleoside capture region able to hybridises selectively to different corresponding second and third oligonucleotides within its particular probe type.

25. The method as claimed in claim 24 wherein up to four different sets of oligonucleotide probe systems are employed, the first oligonucleotide of each set having a nucleoside capture region selective for one of the nucleotide bases of naturally-occurring DNA or RNA and different detectable elements.

26. The method as claimed in claim 14 wherein step (1) further comprises containing each single nucleoside triphosphate in a corresponding microdroplet and steps (2) to (6) are carried out on each microdroplet .

27. The method as claimed in claim 26 wherein the results obtained by step (6) are assembled into a stream of data characteristic of the sequence of the nucleic acid.

* * * * *

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial sequence
<220> FEATURE:
<223> OTHER INFORMATION: oligonucleotide 1
<220> FEATURE:
<221> NAME/KEY: misc_feature
<222> LOCATION: (26)..(26)
<223> OTHER INFORMATION: deoxythymidine nucleotide (T) labelled with
      Atto 655 dye
<220> FEATURE:
<221> NAME/KEY: misc_feature
<222> LOCATION: (27)..(27)
<223> OTHER INFORMATION: deoxythymidine nucleotide (T) labelled with
      Atto 655 dye
<220> FEATURE:
<221> NAME/KEY: misc_feature
<222> LOCATION: (28)..(28)
<223> OTHER INFORMATION: deoxythymidine nucleotide labelled with a BHQ-2
      quencher
<220> FEATURE:
<221> NAME/KEY: misc_feature
<222> LOCATION: (29)..(29)
<223> OTHER INFORMATION: deoxythymidine nucleotide (T) labelled with
      Atto 655 dye
<220> FEATURE:
<221> NAME/KEY: misc_feature
<222> LOCATION: (30)..(30)
<223> OTHER INFORMATION: deoxythymidine nucleotide (T) labelled with
      Atto 655 dye

<400> SEQUENCE: 1
tcgtgcctca tcgaacatga cgaggttttt ggtttgtggt                               40

<210> SEQ ID NO 2
<211> LENGTH: 115
<212> TYPE: DNA
<213> ORGANISM: Artificial sequence
<220> FEATURE:
<223> OTHER INFORMATION: oligonucleotide 2
<220> FEATURE:
<221> NAME/KEY: misc_feature
<222> LOCATION: (1)..(1)
<223> OTHER INFORMATION: 5' phosphate group attached to cytosine

<400> SEQUENCE: 2
catgttcgat gaggcacgat agatgtacgc tttgacatac gctttgacaa tacttgagca        60
gtcggcagat ataggatgtt gcaagctccg tgagtccacc aaaccaaaaa cctcg            115
```